United States Patent
Kiilerich et al.

(10) Patent No.: US 9,732,851 B2
(45) Date of Patent: Aug. 15, 2017

(54) PISTON ROD FOOT

(71) Applicant: Novo Nordisk A/S, Bagsvaerd (DK)

(72) Inventors: Ebbe Kiilerich, Copenhagen NV (DK); Christian Peter Enggaard, Vejby (DK)

(73) Assignee: Novo Nordisk A/S, Bagsvaerd (DK)

( * ) Notice: Subject to any disclaimer, the term of this patent is extended or adjusted under 35 U.S.C. 154(b) by 64 days.

(21) Appl. No.: 14/670,683

(22) Filed: Mar. 27, 2015

(65) Prior Publication Data

US 2015/0198248 A1    Jul. 16, 2015

Related U.S. Application Data

(63) Continuation-in-part of application No. 14/343,149, filed as application No. PCT/EP2012/066696 on Aug. 28, 2012, now Pat. No. 9,101,718.

(60) Provisional application No. 61/532,813, filed on Sep. 9, 2011.

(30) Foreign Application Priority Data

Sep. 6, 2011  (EP) ..................... 11180228

(51) Int. Cl.
    *F16J 1/00*    (2006.01)
    *F16J 9/12*    (2006.01)
    *A61M 5/24*    (2006.01)
    *A61M 5/315*   (2006.01)

(52) U.S. Cl.
    CPC ............... *F16J 1/005* (2013.01); *A61M 5/24* (2013.01); *A61M 5/31513* (2013.01); *A61M 5/31515* (2013.01); *F16J 9/12* (2013.01); *A61M 2205/3372* (2013.01); *A61M 2205/583* (2013.01)

(58) Field of Classification Search
    CPC ................. F16J 1/005; F16J 9/12; F16J 1/006
    See application file for complete search history.

(56) References Cited

U.S. PATENT DOCUMENTS

| 4,145,918 | A  | 3/1979  | Couch et al. |
| 4,191,125 | A  | 3/1980  | Johnson |
| 6,235,004 | B1 | 5/2001  | Steenfeldt-Jensen et al. |
| 8,920,383 | B2 | 12/2014 | Enggaard et al. |

(Continued)

FOREIGN PATENT DOCUMENTS

| CN | 101217989 A | 7/2008 |
| CN | 101227943 A | 7/2008 |
| EP | 774268 A1   | 5/1997 |

(Continued)

*Primary Examiner* — Kevin C Sirmons
*Assistant Examiner* — Deanna K Hall
(74) *Attorney, Agent, or Firm* — Wesley Nicolas

(57) ABSTRACT

The invention relates to a medical drug delivery apparatus which comprises a cartridge (1) being closed at one end by a membrane (12) and at the opposite end by a movable piston (15). A piston rod foot (1) is provided for transferring the pressure from the piston rod (20) of the drug delivery apparatus and onto the piston (15). The piston rod foot (1) comprises a center part (2) abutting the piston rod (20) and an outer part (3) which center part (2) and outer part (3) are coupled together such that the two (2, 3) can be moved relative to one another, yet remain coupled to each other, when a force above a certain threshold limit is applied to the outer part (3).

11 Claims, 4 Drawing Sheets

(56) References Cited

U.S. PATENT DOCUMENTS

2008/0082055 A1* 4/2008 Lloyd ............... A61M 5/31515
                                                            604/218
2015/0038917 A1    2/2015 Nielsen et al.

FOREIGN PATENT DOCUMENTS

| JP | 2004-092671 A | 3/2004 |
| JP | 2008-307237 A | 12/2008 |
| WO | 2007068061 A1 | 6/2007 |
| WO | 2011003979 A1 | 1/2011 |
| WO | 2011/042539 A1 | 4/2011 |

* cited by examiner

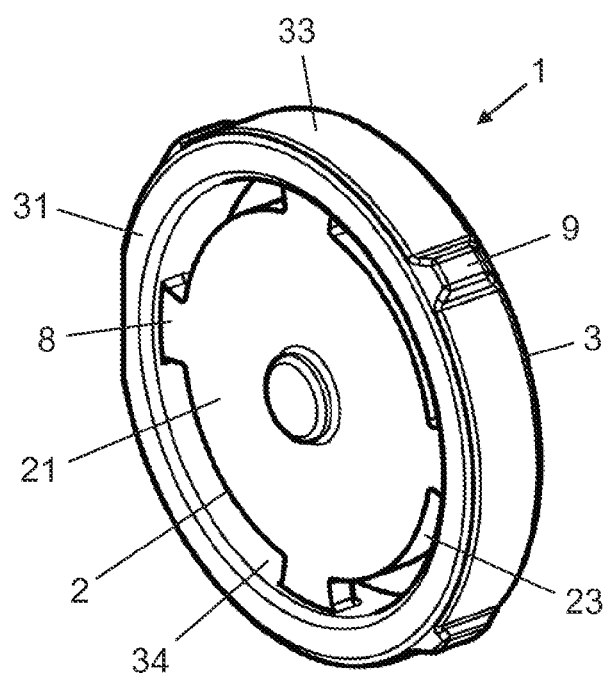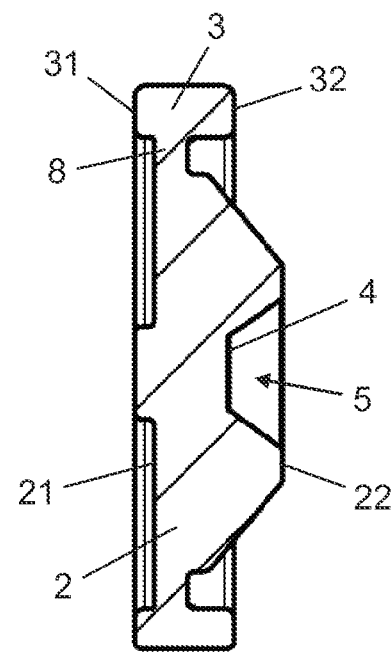
Fig. 4A  Fig. 4B
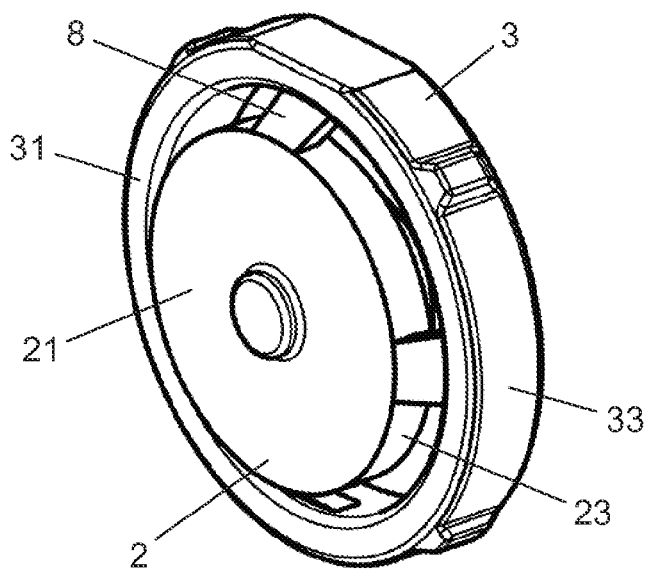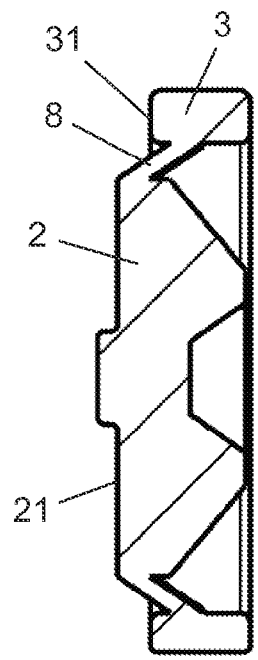
Fig. 5A  Fig. 5B

US 9,732,851 B2

PISTON ROD FOOT

CROSS-REFERENCE TO RELATED APPLICATIONS

This application is a continuation-in-part of U.S. application Ser. No. 14/343,149, filed Apr. 21, 2014, which is a 35 U.S.C. §371 National Stage application of International Application PCT/EP2012/066696 (WO 2013/034467), filed Aug. 28, 2012, which claimed priority of European Patent Application 11180228.6, filed Sep. 6, 2011; this application claims priority under 35 U.S.C. §119 of U.S. Provisional Application 61/532,813; filed Sep. 9, 2011; the contents of the above identified applications are incorporated herein by reference.

THE TECHNICAL FIELD OF THE INVENTION

The invention relates to a medical drug delivery apparatus such as an injection pen in which a piston rod moves a piston or plunger forward inside a cartridge and more specifically the invention relates to a piston rod foot or washer for such injection pen.

DESCRIPTION OF RELATED ART

People suffering from diabetes often have to inject themselves with insulin at a daily basis. For this purpose a great number of different pen systems have been developed over the last 30 years. Common for pen injectors is that they contain a container or cartridge containing the liquid drug to be injected. The cartridge is provided with a piston which is moved forward in order to transfer the liquid drug from the injection pen and into the body of the user.

An example of such commercial successful injection pen, the Flexpen® by Novo Nordisk A/S, is given in U.S. Pat. No. 6,235,004. The cartridge (89) as e.g. depictured in FIG. 15-17 contains the liquid drug to be expelled. At the proximal end the cartridge (89) is closed by a rubber piston which is moved forward inside the cartridge (89) by a piston rod (7). In order to transfer and distribute the force from the piston rod (7) to the rubber piston, a piston rod foot (9) is provided between the piston rod (7) and the rubber piston. The piston rod foot is significantly smaller in diameter than the cartridge interior and the piston sliding inside the cartridge.

For prefilled injection pens which is characterized by the fact that they are discarded when the user has used the prefilled amount of drug there is no possibility for the user to return the piston rod to its initial position. The dosing mechanism is usually constructed such that the piston rod can only move in the distal direction since the injection pen is designed only to be used until the prefilled amount of drug has been used. Further, such injection pens are sealed such that the user can not physically obtain contact with the piston rod. In such injection pens the piston rod foot is normally laying loosely between the rubber piston and the piston rod without being attached to any of the two components since this is the easiest way to assemble the injection pen.

Many pharmaceutical companies prescribe that the liquid drug is stored in a refrigerator or another cold storage facility. However, at the same time many of the liquid drugs available are sensible to frost. The liquid drug should therefore be stored above 0 degrees Celsius at all time. Liquid drugs are often contained in a glass cartridge. If such glass cartridge is exposed to frost not only will the liquid drug be damaged but the liquid will also expand its volume. The increased pressure arising from the expansion can cause the glass of the glass cartridge to fracture if no other possibility for expansion is provided.

WO 2007/068061 (Safety Medical Products Limited) (especially the FIGS. 6 and 7) discloses a container for a liquid drug in which the cap can move axially if the drug is exposed to frost.

In a prefilled injection pen, the piston often cannot move freely in the proximal direction due to the presence of the piston rod which again is used to expel the liquid drug. However, if the piston rod and the piston foot, which are located between the piston rod and the piston, do not obtain the entire area of the surface of the piston, the peripheral portion of the piston can move proximally thereby surrounding the piston rod foot.

In addition, if the radial dimension of the piston washer is smaller than the proximal (or rear) surface area of the piston, the peripheral portion of the piston is allowed to move proximally and thereby deform around the piston washer. This reduces the risk of crack formation in the cartridge wall, but introduces a risk of rubber wedging in between the cartridge wall and the piston washer if the distance therebetween is too small. Conventional piston washers therefore have sufficiently small diameters to prevent the piston from getting stuck.

In order to maximise the dose delivery precision many manufacturers of pen injectors advise that the injection needle remains in the skin for at least six seconds following a finalised dose administration. This is e.g., to give the piston time to relax and resume its normal unstrained state, a process which inevitably leads to an additional expelling of a small volume of the drug through the injection needle. The at least six seconds of extra time to completion of injection is, however, unsatisfactory from a user perspective, and a minimisation of the accumulated flexibility in the dosing system is accordingly desirable. A small diameter piston washer does not contribute positively to this minimisation.

Due to friction between the cartridge wall and the piston during expelling the maximum precision of the size of the injectable dose is obtained if the pressure from piston rod is applied to the piston equally distributed and especially distributed as close to the cartridge wall as possible. However, a large diameter on the piston rod foot, which is preferred in order to distribute the pressure applied at the periphery of the piston, prevents the piston from at least partly move in the proximal direction when exposed to frost thereby increasing the risk for breakage of the glass.

WO 2013/034467 (Novo Nordisk A/S) discloses a drug delivery apparatus with a piston washer comprising a centre part and an outer part which are structured to detach from one another when a force above a certain threshold limit is applied to the outer part. During a normal dose administration the force from the piston rod may thereby be distributed across the entire proximal piston surface, reducing the amount of deformation of the piston and thus the time for subsequent relaxation thereof, while an excessive proximally directed pressure from the piston due to an exposure of the drug delivery apparatus to frost will cause the two piston washer parts to detach, thereby reducing the risk of crack formation as well as providing a clear indication that the device and/or the content of the cartridge may be damaged.

Even if the liquid drug is not damaged by an exposure to frost the entire drug volume will be wasted if the delivery device is either damaged or perceived as damaged and the cartridge cannot be transferred to another delivery device. While the solution presented in WO 2013/034467 provides obvious advantages over the prior art the fact that the peripheral part of the piston washer separates from the centre part and therefore as such becomes an unsupported element in the drug delivery device may potentially confuse a user and lead her/him into concluding that the device is malfunctioning even though its core functions are intact and the device actually is fully functional.

DESCRIPTION OF THE INVENTION

It is an object of the present invention to provide an injection device having a piston rod foot which can transfer the pressure at the periphery of the piston without preventing the piston from moving, at least partly, in the proximal direction should the liquid drug be exposed to frost and expand. It is further an object to provide a build-in freeze-and-thaw indicator indicating to the user whether the drug contained in the injection device has been exposed to frost or not.

In a first embodiment the piston rod foot comprises a centre part and an outer part releasable connected to the centre part. If the liquid contained in the cartridge is frozen, the liquid will expand. This expansion moves the piston in the proximal direction, as the piston which is usually made from a rubber composition is the weakest link. However, the centre part of the piston rod foot abuts the piston rod which is prevented form movement in the proximal direction due to its coupling with the injection mechanism. As a consequence only the part of the piston lying outside the periphery of the centre part of the piston rod foot can move in the proximal direction. This movement moves the outer part of the piston rod foot proximally out of engagement with the centre part of the piston rod foot.

When the injection device is thawed after having been frozen, the piston will move into its non-frozen position and the outer part of the piston rod foot will remain in the position into which it was moved during freezing. This will provide a slightly lesser precision of the injection device, but the injection device will remain workable. A user inspecting the injection device will be able to visible see if the outer part has been dislocated relatively to the centre part.

The releasable coupling between the centre part and the outer part can be formed in any releasable form making it possible for the two parts to disengage when a certain threshold force is surpassed. The centre part and the outer part can be coupled together by breakable elements such as protrusions which break when a the predetermined threshold force is surpassed.

The piston moves the outer part of piston rod foot axially in the proximal direction when the liquid in the cartridge is exposed to frost. In one example of the invention, the centre part and the outer part have different colours such that a user can easily inspect if the outer part has moved relatively to the centre part.

In a further embodiment, the centre part and the outer can have different coefficients of thermal expansion. If the centre part is made from a first material which retracts more during freezing than a second material from which the outer part can be made, then the two parts can decouple fully or partly in the radial direction during freezing.

The piston rod foot is not necessarily provided as a loose part but can be rotatable or non-rotatable hinged to the piston rod. The inner part of the piston rod foot can also be formed integrally with the piston rod if the injection device e.g. is the type in which the piston rod foot do not rotate relatively to the piston rod during dose ejection.

The present invention also involves the piston rod foot comprising a centre part and an outer part releasable coupled together.

In a further embodiment, the centre part and the outer part can be movably coupled to one another, where for example, the centre part and the outer part are physically connected via an axially pliable material.

A piston washer embodying these principles can include a centre part arranged about a centre axis, and an outer part, and the piston washer is capable of transitioning controllably from a first state in which the outer part and the centre part are physically connected and assume a first relative axial position to a second state in which the outer part and the centre part are physically connected and assume a second relative axial position. This allows for the production of a drug delivery device having a piston washer of the same, or substantially the same, diameter as the piston in the drug container, whereby a pressure from the piston rod on the piston washer may be distributed across the entire, or substantially the entire, proximal surface of the piston, reducing the time of relaxation of the piston following a dose administration, while at the same time the piston washer is able to deform by displacement of the outer part relative to the centre part, enabling a volume expansion of the drug substance (with an accompanying peripheral deformation of the piston) that does not cause the container wall to break. During a transition from the first state to the second state the outer part may be permanently axially displaced relative to the centre part, providing a lasting visible indication of the transition.

Thereby, a piston washer for a drug delivery device is provided, the piston washer comprising a centre part arranged, e.g. at least substantially axisymmetrically, about a longitudinal axis, a outer part, and an axially deformable structure connecting the centre part and the outer part, the axially deformable structure being preconfigured, i.e. designed specifically, to deform permanently, e.g. before any other area of the piston washer, in response to a difference between a first resultant force acting on the outer part and a second resultant force acting on the centre part exceeding a threshold level. The axially deformable structure thus constitutes a weakened area and provides for a controlled relative axial displacement between the outer part and the centre part. The axially deformable structure may be configured to exhibit plastic deformation.

Further, the piston washer is configured to transition from a first state in which the outer part and the centre part are physically connected and assume a first relative position along the longitudinal axis to a second state in which the outer part and the centre part are physically connected and assume a second relative position along the longitudinal axis, by deformation of the axially deformable structure, in response to the difference between the first resultant force and the second resultant force exceeding the threshold level. Following the transition from the first state to the second state, when the difference between the first resultant force and the second resultant force falls to or below the threshold level the outer part is permanently axially displaced relative to the centre part.

In other words, the centre part and the outer part remain physically connected during the transition of the piston washer from the first state to the second state. Thereby, when in use no detached portion of the piston washer will move around freely in the drug delivery device at any time, potentially causing concerns as to the dose accuracy of the device. The permanent axial displacement of the outer part relative to the centre part enables a user to visually inspect the current state of the piston washer and thereby get an indication of whether the piston has been transiently deformed and thereby whether the drug delivery device has been exposed to frost.

The centre part may comprise a disc having a proximal surface adapted for abutment with a piston rod in the drug delivery device and a distal surface adapted for abutment with a central piston portion. The outer part may comprise an annular member arranged concentrically about the disc, the annular member comprising a distal surface adapted for abutment with a peripheral piston portion. This provides for symmetry in the construction which in combination with the axisymmetrical load distribution from the piston rod, the piston and the container wall ensures an at least substantially axisymmetrical deformation of the piston washer. It is noted that the annular member may be unitary or segmented, i.e. the annular member need not be formed as a single piece, but may comprise circumferentially spaced apart curved pieces. These curved pieces may be separate or interconnected.

In some embodiments of the invention the axially pliable structure comprises a telescopic tube arranged between the centre part and the outer part. An interior portion of a first tube segment is axially fixed to a radially outwardly directed surface of the centre part, while an exterior portion of a second tube segment is axially fixed to a radially inwardly directed surface of the outer part, and a resistance to relative axial motion between the two tube segments is chosen such that relative axial motion only occurs when the difference between the first resultant force acting on the outer part and the second resultant force acting on the centre part exceeds the threshold level.

In particular embodiments of the invention the centre part and the outer part are radially separated, and the axially pliable structure comprises a plurality of radial bridges which each comprise a first end being connected to a radially inwardly directed surface of the outer part and a second end being connected to a radially outwardly directed surface of the centre part.

The plurality of radial bridges may be evenly distributed along a circumference of the centre part to maintain an axisymmetrical construction. The specific number of radial bridges as well as their respective form may be chosen such that permanent relative axial displacement between the outer part and the centre part only occurs when the difference between the first resultant force acting on the outer part and the second resultant force acting on the centre part exceeds the threshold level.

The axially pliable structure may for example be made of, or at least substantially comprise, polypropylene or polyethylene. In particular, the constituent material may be a PP block copolymer such as SABIC® PP58MNK10.

In particular embodiments of the invention the centre part, the outer part and the axially pliable structure are of the same material, thus providing a fully contained single component solution. A single component piston washer as disclosed herein can be manufactured at a low cost.

The centre part and the outer part may, respectively, have a greater thickness than the axially pliable structure in order to ensure that material deformation only occurs in or at the axially pliable structure.

The outer part may comprise a first rim portion and the centre part may comprise a second rim portion which appears visibly different from the first rim portion. For example, the first rim portion may have a first colour or shade and the second rim portion may have a second colour or shade being different from the first colour or shade. This will enhance the visual evidence of a permanent relative displacement between the outer part and the centre part. The first rim portion may be a portion of, or the entire, radially outwardly directed surface of the outer part and the second rim portion may be a portion of, or the entire, radially outwardly directed surface of the centre part.

The radially outwardly directed surface of the outer part may comprise two or more radially outwardly directed protrusions. The protrusions may thus serve as contact interfaces for an internal drug reservoir wall, while the radially outwardly directed surface of the outer part is separated a small distance from the reservoir wall. The protrusions may be distributed equidistantly along the circumference of the outer part to provide an axisymmetrical support of the piston washer in a drug reservoir.

A segment of the outer part may be flexible, e.g. radially deflectable, to allow a small elastic deformation of the piston washer, e.g. in connection with the initial arrangement thereof in a container vessel having an open end of smaller dimensions than the transversal dimension of the container interior.

The first resultant force may be formed by contributions from e.g. frictional forces between an exterior surface of the outer part and the wall of the drug container, a push force from proximal displacement of the piston periphery, and the material properties and/or configurations of the centre part and the axially pliable structure serving to transfer a share of the force from the piston rod to the outer part. The second resultant force may be formed by contributions from e.g. the piston rod and the piston, being subjected to pressure from the contents of the reservoir. Under normal circumstances, e.g. during administration, the difference between the first resultant force and the second resultant force does not exceed the threshold level, and the piston washer does not undergo any permanent deformation. However, under extreme conditions such as an exposure to frost the force from the expanding drug substance in the reservoir will cause the difference between the first resultant force and the second resultant force to increase and eventually pass the threshold level.

In another aspect of the invention a drug delivery device, e.g. an injection device such as a pen injector, comprising a piston washer as described in the above is provided.

For example, an injection device may be provided comprising: a housing extending along a longitudinal axis, a dose expelling mechanism comprising a piston rod extending between a proximal end portion and a distal end portion, and a piston washer comprising a centre part abutting the distal end portion, a outer part, and an axially pliable structure connecting the centre part and the outer part. The axially pliable structure is preconfigured to undergo permanent deformation in response to a proximally directed force on the outer part exceeding a threshold level. The piston rod is configured to shift between a restricted state in which proximal motion (of the piston rod) relative to the housing is prevented and a free state in which proximal motion (of the piston rod) relative to the housing is allowed. The piston washer is configured to transition permanently, by deformation of the axially pliable structure, from a first state in which the centre part and the outer part are physically connected and assume a first relative axial position to a second state in which the centre part and the outer part are physically connected and assume a second relative axial position in response to the proximally directed force on the outer part transiently exceeding the threshold level, when the piston rod is in the restricted state.

In particular, the outer part may be configured to undergo permanent proximal displacement relative to the centre part in response to the proximally directed force on the outer part transiently exceeding the threshold level.

The outer part and the centre part may be connected by a plurality of bridging structures, and the permanent proximal displacement may be realised by plastic deformation of the bridging structures.

As another example, an injection device may be provided comprising: a) a housing, b) a drug container connected with the housing and comprising a chamber defined by a cylindrical container wall extending along a longitudinal axis, a pierceable septum, and an axially slidable piston having a proximal end surface and a distal end surface, and c) a dose expelling mechanism comprising a piston rod configured for unidirectional distal motion relative to the housing, and a piston washer comprising a centre part abutting the piston rod, a outer part, e.g. at least partially contacting the cylindrical container wall, and an axially pliable structure connecting the centre part and the outer part. The piston washer is arranged to abut the proximal end surface of the piston, and the axially pliable structure is preconfigured to undergo permanent deformation in response to a proximally directed force on the distal end surface of the piston exceeding a threshold level. The piston washer is configured to transition permanently, by deformation of the axially pliable structure, from a first state in which the centre part and the outer part are physically connected and assume a first relative axial position to a second state in which the centre part and the outer part are physically connected and assume a second relative axial position in response to the proximally directed force on the distal end surface of the piston transiently exceeding the threshold level.

This may correspond to a situation where a substance in the chamber freezes and undergoes a volume expansion. The proximally directed force on the piston from the expanding substance is resisted by the piston rod which is prevented from proximal motion relative to the housing. The centre part, being situated between the piston and the piston rod, is thus also prevented from proximal motion relative to the housing, leaving the expansion of the chamber to occur near the container wall, as the piston periphery forces the outer part proximally relative to the centre part.

When the substance in the chamber at some point thaws and accordingly retracts the elastic properties of the piston allows it to resume its original shape, but the piston washer is permanently deformed and does thus not resume its initial shape. The time in which the substance is frozen may be short or long, but in the present context as long as the time is finite the force exceeding the threshold level is transient.

The threshold level may be predetermined by the manufacturer, e.g. by choice of material for and/or design of the piston washer. It is noted, however, that the exact threshold level need not be known by the manufacturer as long as it lies within an interval of threshold levels which ensures that at least ordinary distally directed movements of the piston rod during dose expelling will not cause a permanent displacement of the outer part relative to the centre part and that an expansion of the drug substance due to freezing will. Threshold levels meeting this dual requirement may be identified by experimentation.

The ability of the two parts to release from each other can be provided in multiple of different ways. Either of the parts can be provided with protrusions engaging similar depressions in the opposite part which protrusion breaks when a certain, predetermined threshold force is surpassed in the axial direction. In a different embodiment, the two parts can be provided with a rim and track coupling which are releasable when a certain threshold force is surpassed. This decoupling can be enhanced by the physical shape of the engagement. If the two parts are made from materials having different thermal expansion a decoupling in the radial direction can be facilitated.

DEFINITIONS

An "injection pen" is typically any kind of injection apparatus having an oblong or elongated shape somewhat like a pen for writing. Although such pens usually have a tubular cross-section, they could easily have a different cross-section such as triangular, rectangular or square or any variation around these geometries. Instead of the term "injection apparatus", the term "drug delivery apparatus" or simply "injection device" is also sometimes used with the same meaning. The broad meaning of the term being any kind of device which is able to transfer a liquid to and/or from a person in a subcutaneous way.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

"Cartridge" is the term used to describe the container containing the drug. Cartridges are usually made from glass but could also be moulded from any suitable polymer. A cartridge or ampoule is preferably sealed at one end by a pierceable membrane which can be pierced e.g. by an injection needle. The opposite end is closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. A "piston rod foot" is an element which distributes the force from the piston rod to the movable plunger or piston and is usually located between the piston rod and the movable piston or plunger.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be construed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIGS. 4A and 4B show different views of a piston washer according to another embodiment of the invention before permanent deformation, FIGS. 5A and 5B show different views of the piston washer after permanent deformation.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end pointing towards the needle cannula penetrating the patient whereas the term "proximal end" is meant to refer to the opposite end.

Figure 1:
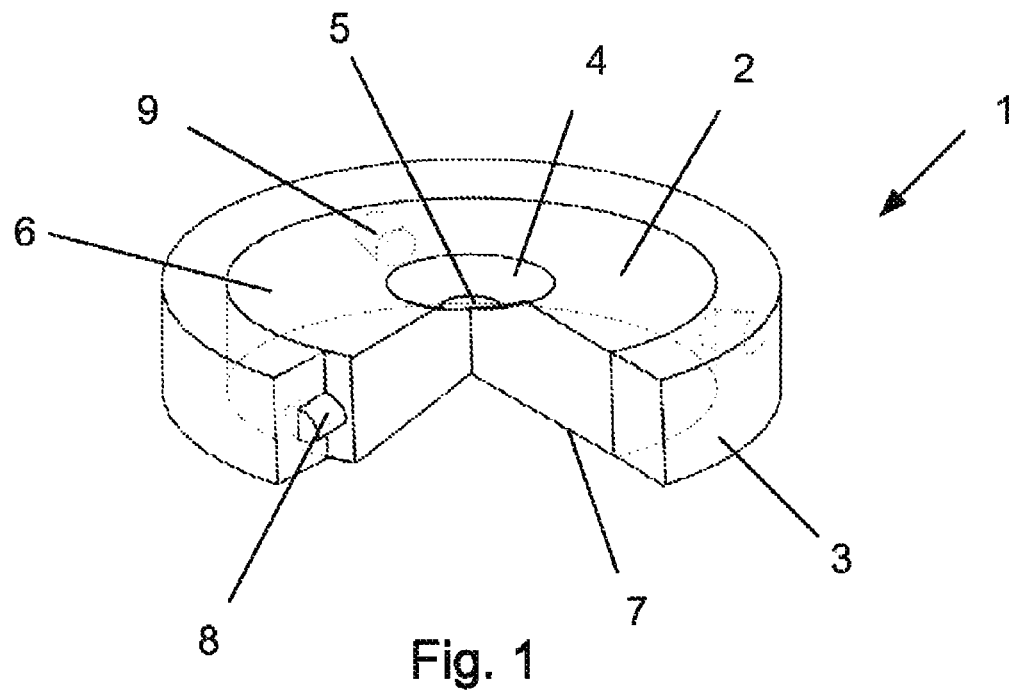
FIG. 1 show an example of the piston rod foot for the drug delivery apparatus according to an embodiment of the invention.

FIG. 1 discloses a piston rod foot 1 for a medical drug delivery apparatus according to the present invention. The piston rod foot 1 comprises a centre part 2 and an outer part 3 which are coupled together. The centre part 2 is in the centre of the proximal surface 6 provided with a circular depression 4 into which a not shown piston rod abut. An opening 5 is provided in the centre of the depression 4. The opposite distal surface 7 abuts the piston 15 (see FIG. 3) during use. The centre part 2 and the outer part 3 are coupled together through a plurality of protrusions 8 in the form of taps engaging similar depression 9. The protrusions 8 are here depictured as being provided on the centre part 2 whereas the depressions 9 are depictured as being provided in the outer part 3. However, this order can be opposite or random.

Figure 2:
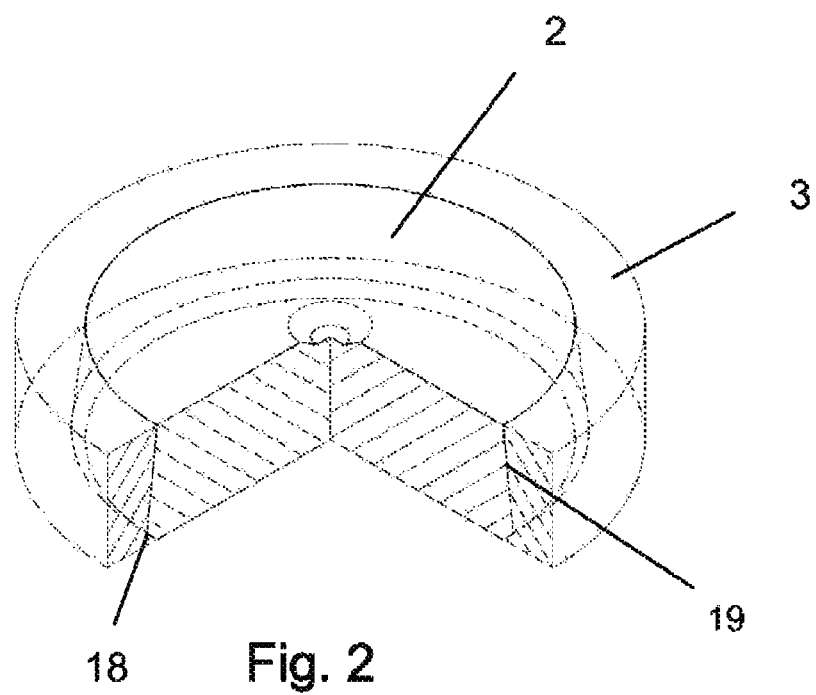
FIG. 2 show another embodiment of the piston rod foot.

FIG. 2 discloses a different embodiment in which the centre part 2 and the outer part 3 engage each other with a V-shaped engagement with one leg in the V being larger than the other such that disengagement are facilitated. The V-shape of the centre part 3 forms a rim 18 circling the centre part 2 and the bottom of the V-shape of the outer part 3 forms a track 19 into which track 19 the rim 18 fits. The centre part 2 and the outer part 3 could also be made from materials having different coefficient of thermal expansion. If e.g. the centre part 2 retracts more than the outer part 3 during freezing, the two parts 2, 3 would fully or partly disengage in the radial direction when exposed to frost.

Figure 3A:
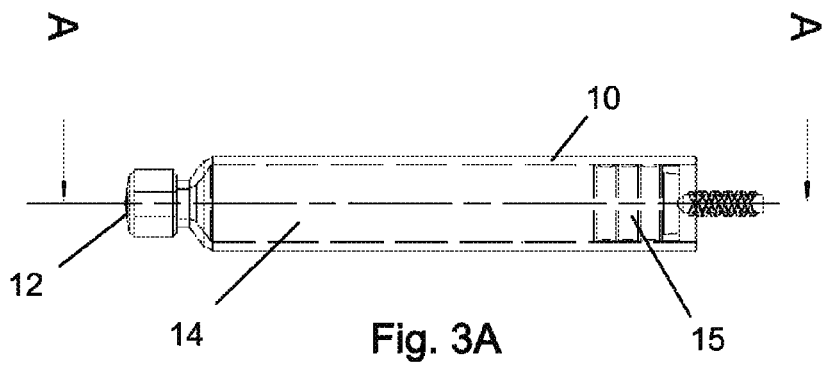
FIGS. 3A-3D shows different views of the piston rod foot inside the cartridge during freezing and thawing of the liquid drug.
Figure 3B:
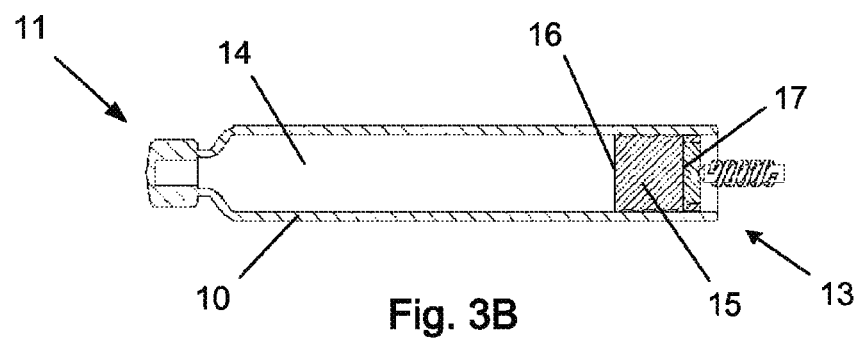
Figure 3C:
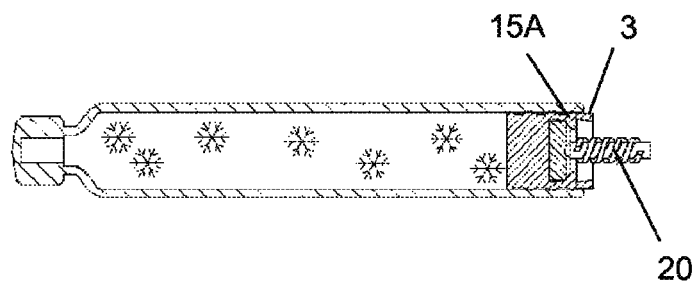
Figure 3D:
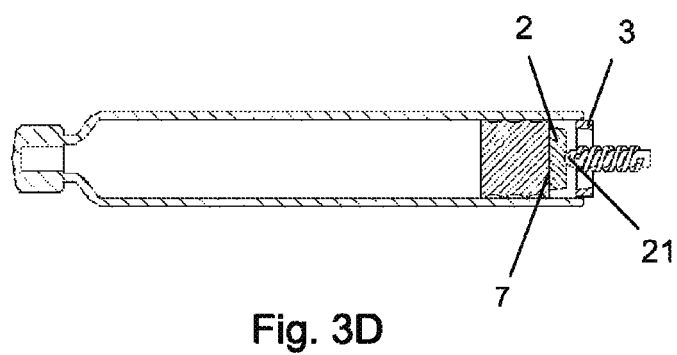

FIGS. 3A-3D discloses a cartridge 10 for the medical drug delivery apparatus according to the invention. FIG. 3B-D is cross sectional views of A-A of FIG. 3A. The cartridge 10 is at its distal end 11 sealed by a membrane 12 which can be penetrated by a not shown injection needle. At the opposite proximal end 13 the cartridge 10 is closed by the movable piston 15. The piston 15 has a front wall 16 which is in contact with the liquid drug encapsulated in the space 14 between the membrane 12 and the front wall 16 of the movable piston 15. Further, the piston 15 has a back wall 17 abutting the distal surface 7 of the piston rod foot 1.

The piston rod 20 is connected to a not shown injection mechanism which moves the piston rod 20 forward during injection. During injection, the distal end 21 of the piston rod 20 abuts the circular depression 4 provided in the proximal surface 6 of the piston rod foot 1. The distal surface 7 of the piston rod foot 1 is in contact with the piston 15 at its back wall 17 such that a force applied to the piston rod 20 is transmitted to the piston 15 via the contact surface between the piston rod foot 1 and the piston 15.

In FIG. 3B the cartridge 10 is disclosed as not exposed to frost. The centre part 2 and the outer part 3 are coupled together and both abut the piston 15 for maximum precision.

If the liquid drug contained inside the cartridge 10 is exposed to frost as disclosed in FIG. 3C, the liquid drug will expand in the space 14 and force the piston 15, which is usually made from rubber in the proximal direction. However, the centre part 2 which is held in its position by the piston rod 20 can not move proximally why only the portion 15A of the piston 15 being peripheral to the centre part 2 will move proximally and thus surround the centre part 2 as illustrated. This movement will be transferred to the outer part 3 which will follow the proximally movement of the peripheral portion 15A of the piston 15 and move out of engagement with the centre part 2. If the centre part 2 and the outer part 3 are secured by protrusions 8 and depressions 9 as indicated in FIG. 1, the protrusions 8 will break as the outer part 2 is moved proximally.

When the liquid drug is thawed, the piston 15 will transform to its original shape as disclosed in FIG. 3D. The centre part 2 will remain in its position abutting the piston 15 and the outer part 3 will remain in the position into which it was moved during freezing. The user of the device can now continue to use the drug delivery device, however with a little less precision since the piston rod foot 1 no longer abuts the piston 15 at its peripheral portion 15A. At the same time the user will be informed that the liquid drug has been exposed to frost due to the new location of the outer part 3.

Since the cartridge 10 is usually embedded in the housing of the drug delivery device this housing can be provided with a window in the position into which the outer part 3 if moved during freezing such that the user just by inspecting the window can obtain information regarding whether the drug delivery device has been exposed to frost or not. The housing could further be equipped with means for securing the outer part 2 in this proximal position. The outer part 3 is preferably coloured in a distinct colour thereby enhancing the visibility of the outer part 3 in the window.

FIGS. 4A and 4B are perspective, respectively cross-sectional views of a piston washer 1 according to another embodiment of the invention in an initial state before permanent deformation. The piston washer 1 comprises a centre portion 2 and an outer portion 3 connected by four bridges 8, each of which extend radially between an exterior surface 23 of the centre portion 2 and an interior surface 34 of the outer portion 3. The centre portion 2 has a distal surface 21 adapted to abut a piston (not shown) during use and a proximal surface 22. The proximal surface 22 is provided with a central depression 5 and has a depressed surface 4 adapted to abut a piston rod (not shown) during use. The outer portion 3 has a distal surface 31 adapted to abut the piston during use and a proximal surface 32. The outer portion 3 further has a circumferential exterior surface 33 along which four protrusions 9 (only three are visible) are distributed. When the piston washer 1 is arranged in a drug cartridge only the protrusions 9 are in contact with an interior cartridge wall, not the entire exterior surface 33. The protrusions 9 are distributed equidistantly along the exterior surface 33, providing for a stable centralised positioning of the piston washer 1. Between each pair of protrusions 9 the exterior surface 33 comprises a flexible zone, enabling easy placement of the piston washer 1, also in a drug cartridge having a proximal end portion of slightly smaller diameter than the maximum radial dimension of the piston washer 1.

In FIGS. 5A and 5B the piston washer 1 is shown in an exemplary state after permanent deformation has occurred. The bridges 8 have undergone plastic deformation during a proximal displacement of the outer portion 3 relative to the centre portion 2, and as a result the distal surface 31 is now positioned proximally of the distal surface 21.

Figure 6:
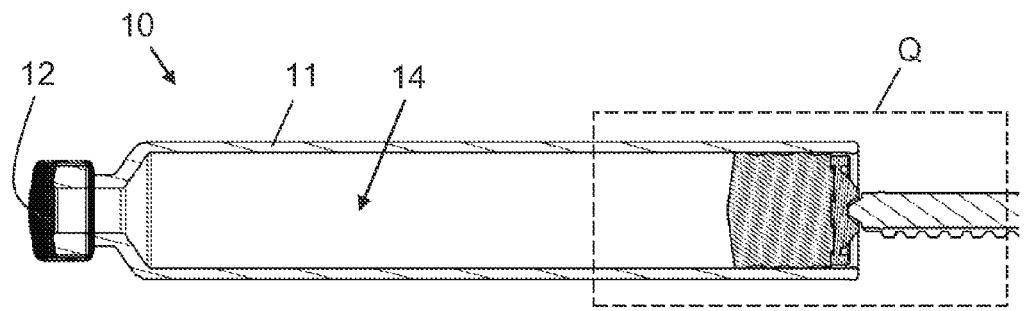
FIG. 6 is a longitudinal cross-section view of the piston washer between a piston rod and a piston in a drug cartridge before permanent deformation of the piston washer.

FIG. 6 is a cross-sectional longitudinal view of a drug cartridge 10 having a generally cylindrical wall 11 and being closed at a distal end by a pierceable rubber septum 12. Opposite thereto a slidable sealing piston 15 (see FIG. 7) is arranged, which together with the septum 12 and the wall 11 defines a closed chamber 14 containing a drug substance (not visible). The cartridge 10 forms part of a drug delivery device (not shown), and is shown in a pre-use state before any drug expelling has taken place.

Figure 7:
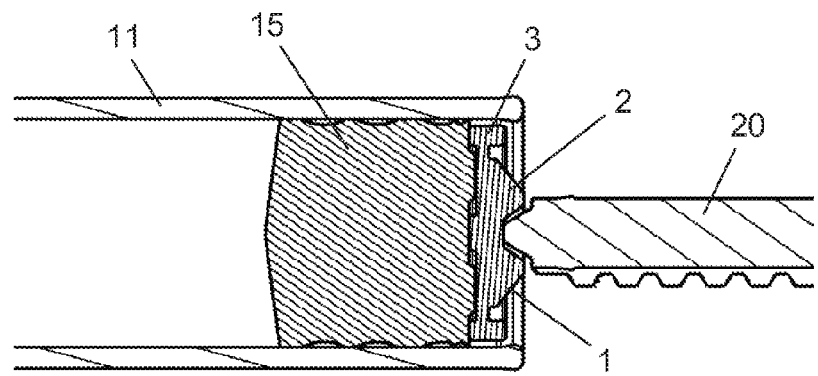
FIG. 7 is a close up of a proximal section of the drug cartridge of FIG. 6.

FIG. 7 is a close up of a proximal section of the cartridge 10 as delimited by the area Q in FIG. 6, showing the piston washer 1 arranged at a proximal end of the wall 11 between the piston 15 and a piston rod 20. It is noted that the piston washer 1 contacts the piston 15 across substantially the entire proximal surface of the piston 15, thereby enabling a distribution of the distally directed force from the piston rod 20 during a dose administration also to a peripheral portion 15A (see FIG. 8) of the piston 15.

Figure 8:
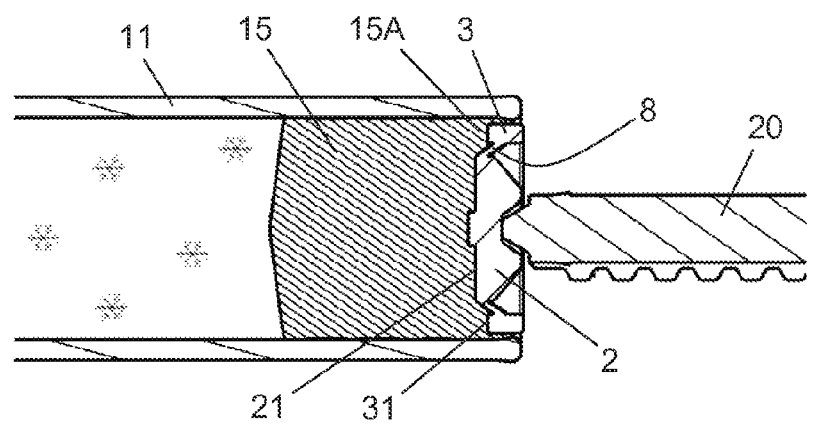
FIG. 8 shows the proximal section of the drug cartridge in frosty conditions after deformation of the piston washer.

FIG. 8 shows what happens if the cartridge 10 is e.g. exposed to frost. In that case, given that the piston rod 20 is supported by a delivery mechanism in the drug delivery device and thus cannot move proximally, the proximally directed force on the piston 15 from the drug expanding in the chamber 14 will force the bridges to deform and the outer portion 3 to displace axially in the proximal direction, thereby allowing the peripheral portion 15A of the piston 15 to crawl up around the centre portion 2 in response. When the force exceeds a certain threshold the bridges 8 begin to yield making permanent room for the drug and providing the needed volume expansion of the chamber 14. Cracking of the cartridge wall 11 is thus avoided.

Figure 9:
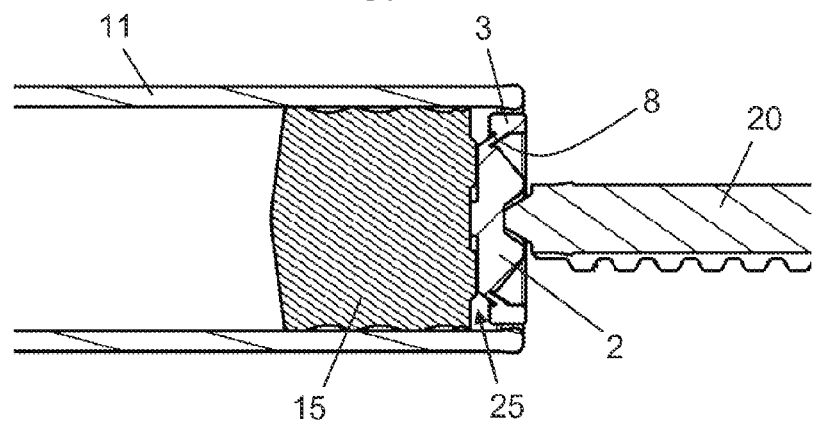
FIG. 9 shows the proximal section of the drug cartridge after thawing of the drug.

FIG. 9 shows the cartridge 10 after thawing of the drug in the chamber 14. The outer portion 3 is permanently displaced relative to the centre portion 2 due to the plastic deformation of the bridges 8, leaving an air gap 25 between the distal surface 31 and the piston 15. Regardless of the usability of the drug the drug delivery device can still be used to administer doses of the drug as before. However, the time to completion of a dose may have increased due to the lacking support on the piston by the outer portion 3.

The axial displacement of the outer portion 3 relative to the centre portion 2 provides a visual indication that the drug has potentially been exposed to frost. Hence, it is possible for an examiner of a customer complaint to verify whether drug freezing may have been a reason for the complaint or not. The exterior surface 23 may be configured to appear visibly different from the exterior surface 33, e.g. by having a different colour, such that the relative displacement of the outer portion 3 and the centre portion 2 is even more clearly identifiable.

Some preferred embodiments have been shown in the foregoing, but it should be stressed that the invention is not limited to these, but may be embodied in other ways within the subject matter defined in the following claims.

The invention claimed is:

1. A piston washer (1) for a drug delivery device, the piston washer (1) comprising:
a centre part (2) arranged about a centre axis,
a outer part (3), and
an axially pliable structure (8) connecting the centre part (2) and the outer part (3), the axially pliable structure (8) being preconfigured to undergo permanent deformation in response to a difference between a first resultant force acting on the outer part (3) and a second resultant force acting on the centre part (2) exceeding a threshold level,
wherein the piston washer (1) is configured to transition permanently by deformation of the axially pliable structure (8) from a first state in which the centre part (2) and the outer part (3) are physically connected and assume a first relative axial position to a second state in which the centre part (2) and the outer part (3) are physically connected and inseparable and assume a second relative axial position in response to the difference between the first resultant force and the second resultant force transiently exceeding the threshold level.

2. A piston washer according to claim 1, wherein the centre part (2) comprises a disc and the outer part (3) comprises an annular member arranged concentrically about the disc.

3. A piston washer according to claim 1, wherein the axially pliable structure (8) is configured to exhibit plastic deformation.

4. A piston washer according to claim 1, wherein the centre part (2) and the outer part (3) are radially separated, and
wherein the axially pliable structure (8) comprises a plurality of radial bridges, each of the plurality of radial bridges comprising a first end being connected to a radially inwardly directed surface (34) of the outer part (3) and a second end being connected to a radially outwardly directed surface (23) of the centre part (2).

5. A piston washer according to claim 4, wherein the plurality of radial bridges are evenly distributed along a circumference of the centre part (2).

6. A piston washer according to claim 1, wherein the axially pliable structure (8) is made of a PP block copolymer.

7. A piston washer according to claim 1, wherein the centre part (2), the outer part (3) and the pliable structure (8) are of the same material.

8. A piston washer according to claim 1, wherein at least a rim of the centre part (2) has a first colour or shade and at least a rim of the outer part (3) has a second colour or shade, the second colour or shade being different from the first colour or shade.

9. A piston washer according to claim 1, wherein a segment of the outer part (3) is flexible, and
   wherein at least two radially outwardly directed surface portions of the outer part (3) comprises a radially outwardly directed protrusion (9).

10. A drug delivery device comprising a piston washer (1) according to claim 1.

11. A drug delivery device according to claim 10, further comprising:
   a drug reservoir (10) comprising a chamber (14) defined by
      a reservoir body (11),
      a penetrable septum (12) closing a first portion of the reservoir body (11), and
      a piston (15) closing a second portion of the reservoir body (11), and
   a piston rod (20) for moving the piston (15) towards the penetrable septum (12),
   wherein at least a portion of the centre part (2) is arranged between the piston rod (20) and the piston (15).

* * * * *